(12) United States Patent
Osumi et al.

(10) Patent No.: US 10,143,439 B2
(45) Date of Patent: Dec. 4, 2018

(54) ULTRASOUND DIAGNOSIS APPARATUS, IMAGE PROCESSING APPARATUS, AND IMAGE PROCESSING METHOD

(71) Applicant: Toshiba Medical Systems Corporation, Otawara-shi (JP)

(72) Inventors: Ryota Osumi, Nasushiobara (JP); Tetsuya Kawagishi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 771 days.

(21) Appl. No.: 14/518,036

(22) Filed: Oct. 20, 2014

(65) Prior Publication Data

US 2015/0119711 A1    Apr. 30, 2015

(30) Foreign Application Priority Data

Oct. 31, 2013   (JP) .................................. 2013-227497

(51) Int. Cl.
*A61B 8/08*   (2006.01)
*A61B 8/00*   (2006.01)

(52) U.S. Cl.
CPC .......... *A61B 8/4416* (2013.01); *A61B 8/5215* (2013.01); *A61B 8/5253* (2013.01);
(Continued)

(58) Field of Classification Search
CPC ... A61B 8/4416; A61B 8/5215; A61B 8/5253; A61B 8/485; A61B 8/488; A61B 8/5223
See application file for complete search history.

(56) References Cited

U.S. PATENT DOCUMENTS 7,664,301 B2   2/2010   Kim et al.
8,202,221 B2   6/2012   Osumi et al.
(Continued)

FOREIGN PATENT DOCUMENTS

| JP | 2006-116307 | 5/2006 |
| JP | 2009-153918 | 7/2009 |
| JP | 2011-56249 A | 3/2011 |

OTHER PUBLICATIONS

Office Action dated Apr. 18, 2017 in Japanese Patent Application No. 2013-227497.

*Primary Examiner* — Pascal M Bui Pho
*Assistant Examiner* — Colin T Sakamoto
(74) *Attorney, Agent, or Firm* — Oblon, McClelland, Maier & Neustadt, L.L.P.

(57) ABSTRACT

An ultrasound diagnosis apparatus includes: a transmitting and receiving unit that transmits and receives an ultrasound wave to and from a subject; a first image data generating unit that generates first image data based on a first parameter, from a reception signal received by the transmitting and receiving unit; a second image data generating unit that generates second image data having an image taking region of which at least a part overlaps with that of the first image data and being based on a second parameter that is different from the first parameter, from a reception signal received by the transmitting and receiving unit; and an image processing unit that calculates a feature amount from at least such a part of the second image data that overlaps with the first image data and corrects the overlapping part of the first image data on a basis of the calculated feature amount.

6 Claims, 11 Drawing Sheets

(52) U.S. Cl.
CPC .............. *A61B 8/485* (2013.01); *A61B 8/488* (2013.01); *A61B 8/5223* (2013.01)

(56) References Cited

U.S. PATENT DOCUMENTS

| | | | |
|---|---|---|---|
| 2008/0021326 A1* | 1/2008 | Bakircioglu | A61B 8/06 600/454 |
| 2008/0077011 A1* | 3/2008 | Azuma | G06T 7/215 600/443 |
| 2009/0112088 A1* | 4/2009 | Ohuchi | A61B 6/5282 600/438 |
| 2009/0171208 A1* | 7/2009 | Osumi | A61B 8/08 600/443 |
| 2011/0040183 A1 | 2/2011 | Yoshida | |
| 2012/0330155 A1* | 12/2012 | Jiang | A61B 8/08 600/438 |

* cited by examiner

ULTRASOUND DIAGNOSIS APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2013-227497, filed on Oct. 31, 2013; the entire contents of which are incorporated herein by reference.

FIELD

Embodiments described herein relate generally to an ultrasound diagnosis apparatus, an image processing apparatus, and an image processing method.

BACKGROUND

Conventionally, an ultrasound diagnosis apparatus emits ultrasound wave pulses generated by ultrasound transducer elements provided in an ultrasound probe to the inside of an examined subject and receives reflected-wave signals from a tissue of the subject through the ultrasound transducer elements. Further, the ultrasound diagnosis apparatus generates image data from the reflected-wave signals and generates and displays an ultrasound image generated from the image data.

Various types of image filters are applied to the image data for the purpose of reducing noise and speckles, or the like. For example, an image filter detects edge sizes and directions as feature amounts of an image and smooths the image or controls the degree of enhancement on the basis of the detected directions.

DETAILED DESCRIPTION

An ultrasound diagnosis apparatus according to an embodiment includes a transmitting and receiving unit, a first image data generating unit, a second image data generating unit, and an image processing unit. The transmitting and receiving unit transmits and receives an ultrasound wave to and from a subject. The first image data generating unit generates first image data based on a first parameter, from a reception signal received by the transmitting and receiving unit. The second image data generating unit generates second image data having an image taking region of which at least a part overlaps with that of the first image data and being based on a second parameter that is different from the first parameter, from a reception signal received by the transmitting and receiving unit. The image processing unit calculates a feature amount from at least such a part of the second image data that overlaps with the first image data and corrects such a part of the first image data that overlaps with the second image data on the basis of the calculated feature amount.

Exemplary embodiments of an ultrasound diagnosis apparatus, an image processing apparatus, and an image processing method will be explained below, with reference to the accompanying drawings.

First Embodiment

Figure 1:
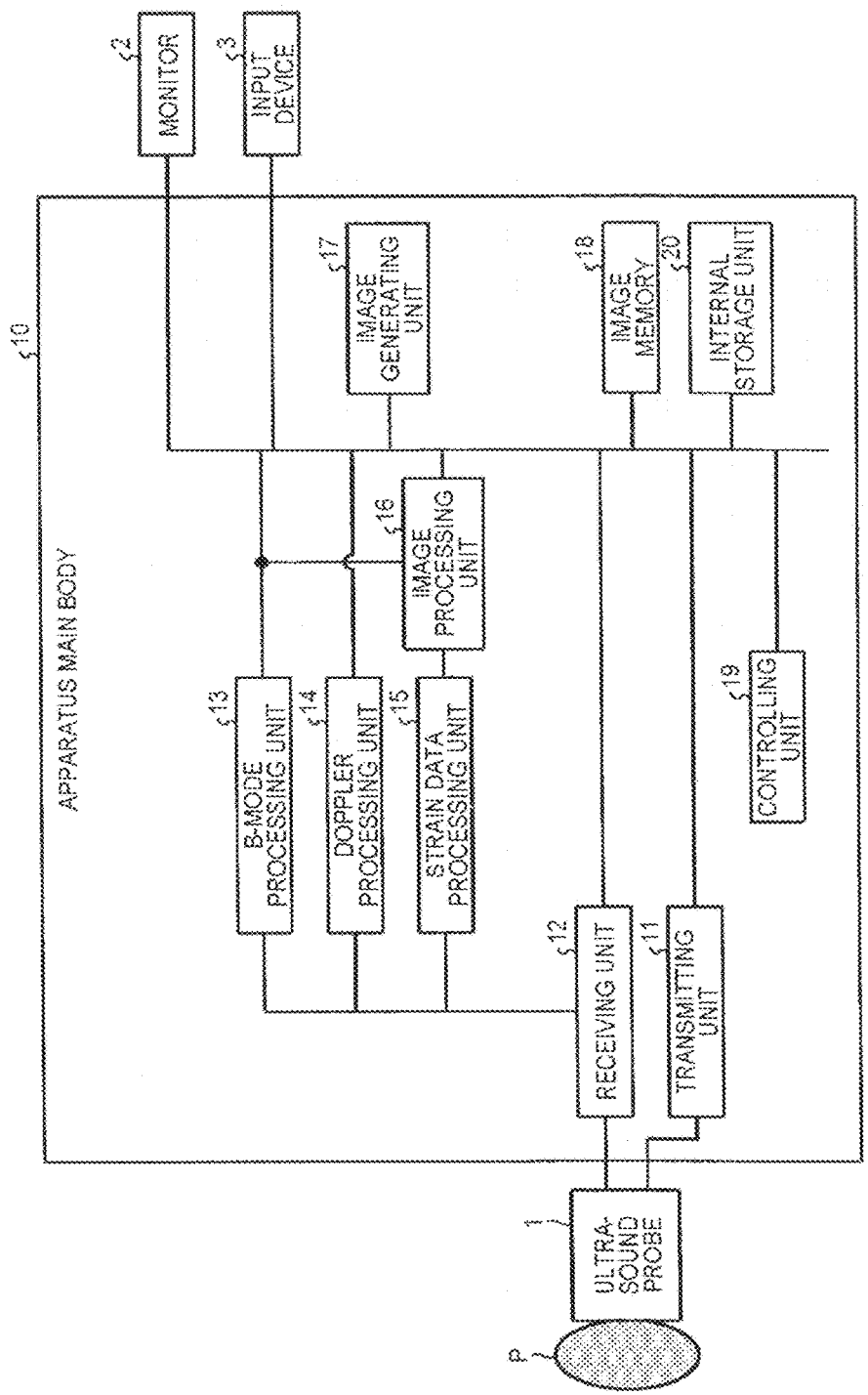
FIG. 1 is a drawing for explaining an overall configuration of an ultrasound diagnosis apparatus according to a first embodiment.

First, a configuration of an ultrasound diagnosis apparatus according to a first embodiment will be explained. FIG. 1 is a drawing for explaining an overall configuration of an ultrasound diagnosis apparatus according to the first embodiment. As illustrated in FIG. 1, the ultrasound diagnosis apparatus according to the first embodiment includes an ultrasound probe 1, a monitor 2, an input device 3, and an apparatus main body 10.

The ultrasound probe 1 includes a plurality of piezoelectric transducer elements, which generate an ultrasound wave on the basis of a drive signal supplied from a transmitting unit 11 included in the apparatus main body 10 (explained later). Further, the ultrasound probe 1 receives a reflected wave from an examined subject P and converts the received reflected wave into an electric signal. Further, the ultrasound probe 1 includes matching layers and acoustic lenses included in the piezoelectric transducer elements, as well as a backing member that prevents ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift (a Doppler shift), depending on a velocity component of the moving members with respect to the ultrasound wave transmission direction.

The first embodiment is applicable to a situation where the ultrasound probe 1 is configured as a one-dimensional ultrasound probe in which the plurality of piezoelectric transducer elements are arranged in a row so as to scan (two-dimensionally scan) a two-dimensional region inside the subject P and to a situation where the ultrasound probe 1 is configured as a one-dimensional ultrasound probe in which the plurality of piezoelectric transducer elements are mechanically caused to swing or is configured as a two-dimensional ultrasound probe in which the plurality of piezoelectric transducer elements are two-dimensionally arranged in a grid formation, so as to scan (three-dimensionally scan) a three-dimensional region inside the subject P.

The input device 3 includes a mouse, a keyboard, a button, a panel switch, a touch command screen, a foot switch, a trackball, and the like. The input device 3 receives various types of setting requests from an operator of the ultrasound diagnosis apparatus and transfers the received various types of setting requests to the apparatus main body 10.

The monitor 2 displays a Graphical User Interface (GUI) used by the operator of the ultrasound diagnosis apparatus to input the various types of setting requests through the input device 3 and displays an ultrasound image and the like generated by the apparatus main body 10.

The apparatus main body 10 is an apparatus that generates the ultrasound image on the basis of the reflected waves received by the ultrasound probe 1. As illustrated in FIG. 1, the apparatus main body 10 includes the transmitting unit 11, a receiving unit 12, a B-mode processing unit 13, a Doppler processing unit 14, a strain data processing unit 15, an image processing unit 16, an image generating unit 17, an image memory 18, a controlling unit 19, and an internal storage unit 20.

The transmitting unit 11 includes a trigger generating circuit, a transmission delaying circuit, a pulser circuit, and the like and supplies the drive signal to the ultrasound probe 1. The pulser circuit repeatedly generates a rate pulse for forming a transmission ultrasound wave at a predetermined rate frequency. Further, the transmission delaying circuit applies a delay period that is required to converge the ultrasound wave generated by the ultrasound probe 1 into the form of a beam and to determine transmission directionality and that corresponds to each of the piezoelectric transducer elements, to each of the rate pulses generated by the pulser circuit. Further, the trigger generating circuit applies a drive signal (a drive pulse) to the ultrasound probe 1 with timing based on the rate pulses. In other words, the transmission delaying circuit arbitrarily adjusts the transmission directions from the piezoelectric transducer element surfaces, by varying the delay periods applied to the rate pulses.

The transmitting unit 11 has a function to be able to instantly change the transmission frequency, the transmission drive voltage, and the like, for the purpose of executing a predetermined scanning sequence on the basis of an instruction from the controlling unit 19 (explained later). In particular, the configuration to change the transmission drive voltage is realized by using a linear-amplifier-type transmitting circuit of which the value can be instantly switched or by using a mechanism that electrically switches between a plurality of power source units.

The receiving unit 12 includes an amplifying circuit, an Analog/Digital (A/D) converter, an adder, and the like and generates reflected-wave data by performing various types of processes on the reflected-wave signal received by the ultrasound probe 1. The amplifying circuit performs a gain correction process by amplifying the reflected-wave signal for each of channels. The A/D converter applies an A/D conversion to the gain-corrected reflected-wave signal and applies a delay period required to determine reception directionality to the digital data. The adder performs an adding process on the reflected-wave signals processed by the A/D converter, so as to generate the reflected-wave data. As a result of the adding process performed by the adder, reflected components from the direction corresponding to the reception directionality of the reflected-wave signals are emphasized.

In the manner described above, the transmitting unit 11 and the receiving unit 12 control the transmission directionality and the reception directionality in the ultrasound wave transmissions and receptions.

In this situation, when the ultrasound probe 1 is capable of performing a three-dimensional scan, the transmitting unit 11 and the receiving unit 12 are also able to cause the ultrasound probe 1 to transmit ultrasound beams toward a three-dimensional region inside the subject P and to generate reflected-wave data corresponding to a plurality of positions within a three-dimensional space, from reflected-wave signals that correspond to the plurality of positions within the three-dimensional space and that are received by the ultrasound probe 1.

The B-mode processing unit 13 receives the reflected-wave data from the receiving unit 12 and generates data ("B-mode data" or "B-mode image data") in which the strength of each signal is expressed by a degree of brightness, by performing a logarithmic amplification, an envelope detection process, and the like on the received reflected-wave data.

The Doppler processing unit 14 obtains velocity information from the reflected-wave data received from the receiving unit 12 by performing a frequency analysis, to extract bloodstream, tissues, and contrast-agent echo components under the influence of the Doppler effect, and further generates data ("Doppler data" or "Doppler image data") obtained by extracting moving member information such as an average velocity, a dispersion, a power, and the like, for a plurality of points. More specifically, the Doppler processing unit 14 generates the Doppler data by extracting the average velocity, dispersion values, power values and the like for the plurality of points, as movement information of the moving members. Even more specifically, the Doppler processing unit 14 generates color Doppler data used for generating a color Doppler image indicating dynamics of the bloodstream and generates tissue Doppler data used for generating a tissue Doppler image indicating dynamics of the tissues.

The B-mode processing unit 13 and the Doppler processing unit 14 according to the first embodiment are able to process both reflected-wave data corresponding to a plurality positions within a two-dimensional space and reflected-wave data corresponding to a plurality of positions within a three-dimensional space. In other words, the B-mode processing unit 13 is able to generate B-mode data corresponding to a plurality of positions within a two-dimensional space from reflected-wave data corresponding to the plurality of positions within the two-dimensional space and is also able to generate B-mode data corresponding to a plurality of positions within a three-dimensional space from reflected-wave data corresponding to the plurality of positions within the three-dimensional space. Further, the Doppler processing unit 14 is able to generate Doppler data corresponding to a plurality of positions within a two-dimensional space from reflected-wave data corresponding to the plurality of positions within the two-dimensional space and is also able to generate Doppler data corresponding to a plurality of positions within a three-dimensional space from reflected-wave data corresponding to the plurality of positions within the three-dimensional space.

The strain data processing unit 15 calculates strains expressing hardness of a tissue from the reflected-wave data received from the receiving unit 12 and generates strain data indicating a spatial distribution of the strains. For example, when an elastography mode in which elastography is implemented is specified, the strain data processing unit 15 calculates the strains from the reflected-wave data and generates the strain data. Elastography is a technique used for imaging elasticity of a tissue.

One of known methods for calculating a strain is a method by which a strain value is calculated by detecting a displacement of a tissue between adjacent frames on the basis of a cross-correlation between pieces of reflected-wave data. As the method for calculating the strains, the strain data processing unit 15 is able to implement any of various methods.

In the following sections, an example will be explained in which, when the elastography mode is specified, the operator manually applies shaking movements to the ultrasound probe 1 so as to repeatedly press and release a tissue, so that the strain data processing unit 15 calculates the strain values by detecting a displacement of the tissue between adjacent frames on the basis of a cross-correlation between pieces of reflected-wave data. In the elastography mode, there are situations where, for example, the strain data processing unit 15 calculates strains on the basis of a distortion (a change in the shape) of a tissue caused by a small movement of the hand of the operator holding the ultrasound probe 1.

More specifically, the strain data processing unit 15 calculates a displacement of a tissue in the subject's body distorted due to the ultrasound probe 1 being lightly pressed against and released from the body surface of the subject P by a hand of the operator while being in contact therewith. Even more specifically, the strain data processing unit 15 calculates a displacement of mutually the same site position, by using two or more pieces of reflected-wave data that are obtained before and after the distortion or that have mutually-different degrees of distortion. After that, the strain data processing unit 15 calculates a strain value by differentiating the displacement in the depth direction. In this situation, the harder a tissue is, the less easily the tissue changes the shape thereof (the less easily the tissue gets distorted). Accordingly, the strain value of a harder tissue is smaller, whereas the strain value of a softer tissue in the subject's body is larger. In the following explanation, the strain data generated by the strain data processing unit 15 may be referred to as "strain image data".

The image processing unit 16 performs various types of image processing processes on ultrasound image data. In the first embodiment, for example, by performing a filtering process combining a multi-resolution analysis with a non-linear anisotropic diffusion filter on the ultrasound image data, the image processing unit 16 performs an image processing process (a smoothing process) to re-generate an average-brightness-value image, an image processing process (an edge enhancement process) that employs a differential filter within the image, a speckle eliminating process, and the like. Processes performed by the image processing unit 16 according to the first embodiment will be explained in detail later.

The image generating unit 17 generates a display-purpose ultrasound image by using the data generated by the B-mode processing unit 13, the Doppler processing unit 14, and the strain data processing unit 15. In other words, from the B-mode data generated by the B-mode processing unit 13, the image generating unit 17 generates a B-mode image in which the strength of the reflected wave is expressed by a degree of brightness. Further, from the Doppler data generated by the Doppler processing unit 14, the image generating unit 17 generates a Doppler image (a color Doppler image or a tissue Doppler image) such as an average velocity image, a dispersion image, a power image, or an image combining these images that expresses the moving member information (e.g., bloodstream movement information, tissue movement information).

Further, the image generating unit 17 generates an elastography image by using the strain data generated by the strain data processing unit 15. More specifically, the image generating unit 17 generates the elastography image by generating a strain image in which the level of gray scale is varied in accordance with the strain value calculated for each of the window widths and superimposing the generated strain image onto a B-mode image. In this situation, when generating the elastography image, the image generating unit 17 generates a display-purpose ultrasound image by using the data on which any of the various types of image processing processes has been performed by the image processing unit 16.

In this situation, generally speaking, the image generating unit 17 converts (by performing a scan convert process) a scanning line signal sequence from an ultrasound scan into a scanning line signal sequence in a video format used by, for example, television and generates the ultrasound image serving as a display-purpose image. More specifically, the image generating unit 17 generates the ultrasound image serving as a display-purpose image by performing a coordinate transformation process compliant with the ultrasound scanning mode used by the ultrasound probe 1.

Further, the image generating unit 17 has installed therein a storage memory for storing image data therein and is capable of performing a three-dimensional image reconstructing process and the like. Further, from the storage memory installed in the image generating unit 17, for example, the operator is able to invoke images recorded during medical examinations after a diagnosis process.

Further, the image generating unit 17 synthesizes text information of various parameters, scale graduations, body marks, and the like with the generated ultrasound image data and further outputs the synthesized image data to the monitor 2 as video signals. Further, the image generating unit 17 is also capable of generating synthesized image data in which a plurality of pieces of image data are superimposed with one another. In other words, the data generated by the B-mode processing unit 13, the Doppler processing unit 14, and the strain data processing unit 15 is ultrasound image data before the scan covert process, whereas the data generated by the image generating unit 17 is display-purpose ultrasound image data after the scan covert process. The various types of data generated by the B-mode processing unit 13, the Doppler processing unit 14, and the strain data processing unit 15 may be referred to as "raw data".

The image memory 18 stores therein the ultrasound image and the synthesized image generated by the image generating unit 17. Further, the image memory 18 is also able to store therein the data (the raw data) generated by the B-mode processing unit 13, the Doppler processing unit 14, and the strain data processing unit 15. Furthermore, the image memory 18 is also able to store therein the data on which any of the various types of image processing processes has been performed by the image processing unit 16.

The internal storage unit 20 stores therein control computer programs (hereinafter, "control programs") to realize ultrasound transmissions and receptions, image processing, and display processing, as well as various types of data such as diagnosis information (e.g., subject s'IDs, medical doctors' observations), diagnosis protocols, and various types of body marks. Further, the internal storage unit 20 may be used, as necessary, for storing therein any of the images stored in the image memory 18. Further, it is possible to transfer the data stored in the internal storage unit 20 to an external peripheral apparatus via an interface (not shown).

The controlling unit 19 controls the entire processes performed by the ultrasound diagnosis apparatus. More specifically, on the basis of the various types of setting requests input by the operator via the input device 3 and the various types of control programs and the various types of data read from the internal storage unit 20, the controlling unit 19 controls processes performed by the transmitting unit 11, the receiving unit 12, the B-mode processing unit 13, the Doppler processing unit 14, the strain data processing unit 15, the image processing unit 16, and the image generating unit 17. Further, the controlling unit 19 exercises control so that the monitor 2 displays the ultrasound images and the synthesized images stored in the image memory 18 and the GUI used by the operator to specify any of the various types of processes.

An overall configuration of the ultrasound diagnosis apparatus according to the first embodiment has thus been explained. The ultrasound diagnosis apparatus according to the first embodiment configured as described above performs an ultrasound image taking process through ultrasound wave transmissions and receptions.

The filtering process performed by the image processing unit 16 is applicable not only to the B-mode data but also to images in other modes. For example, as an example of the filtering process, the image processing unit 16 decomposes the strain data, by performing a multi-resolution decomposition, into low-range decomposed image data and high-range decomposed image data on a predetermined number of hierarchical levels (a predetermined number of levels) by performing a wavelet transformation process. After that, the image processing unit 16 sequentially processes the image data from the image data on the lowest level to the image data on the highest level, by using the non-linear anisotropic diffusion filter.

Figure 2:
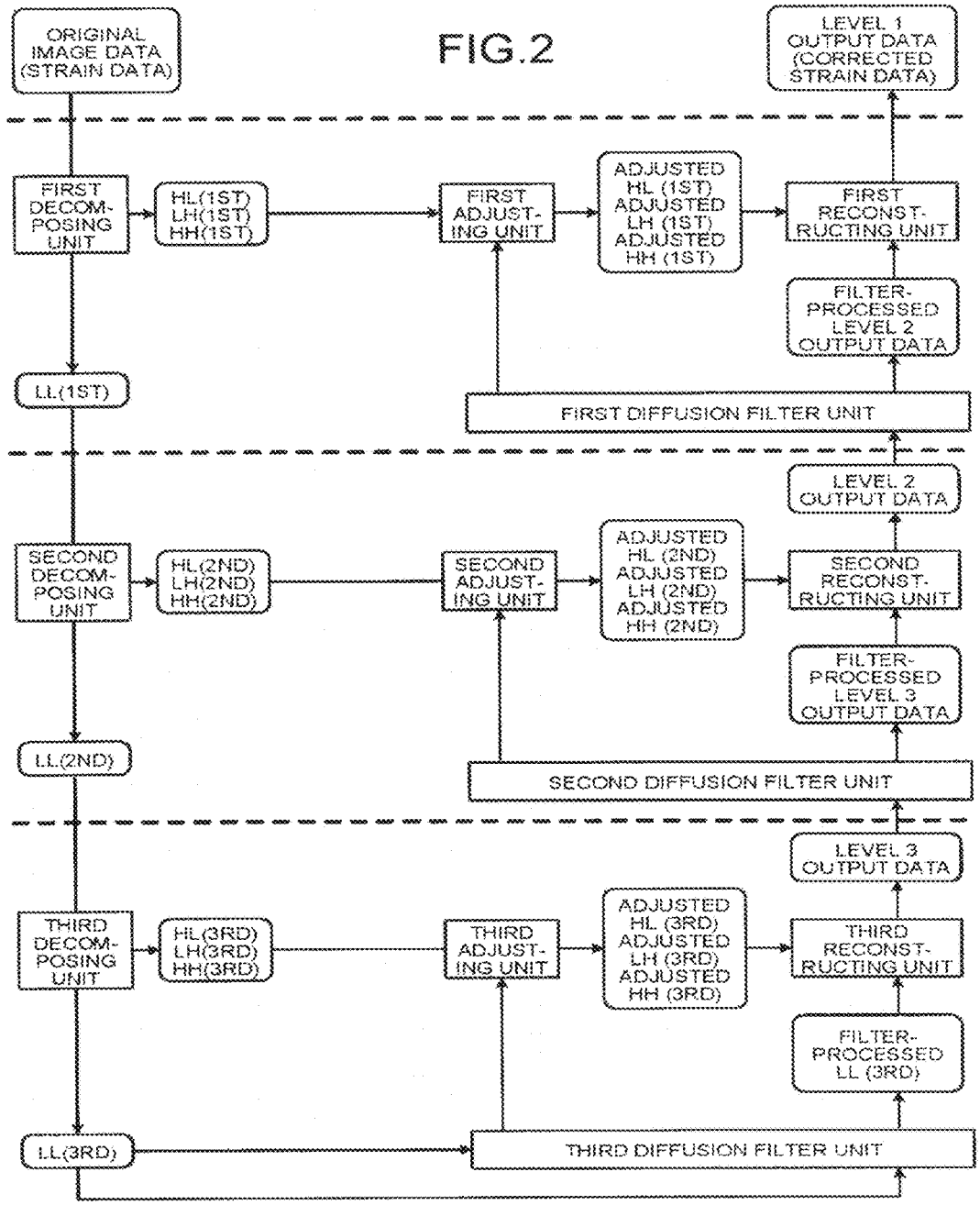
FIG. 2 is a drawing for explaining a conventional method.

FIG. 2 is a drawing for explaining a conventional method. In the example illustrated in FIG. 2, original image data serving as a processing target of an image processing unit is strain data generated by a strain data processing unit. Further, FIG. 2 illustrates a situation where the number of levels in a multi-resolution analysis is "3".

The image processing unit according to the conventional method includes a decomposing unit, a diffusion filter unit, an adjusting unit, and a reconstructing unit, on each of the levels. For the sake of convenience in the explanation, when it is necessary to distinguish the decomposing units, the diffusion filter units, the adjusting units, and the reconstructing units on the different levels from one another, the functional units may be referred to as follows: The functional units on level 1 will be referred to as a first decomposing unit, a first diffusion filter unit, a first adjusting unit, and a first reconstructing unit; the functional units on level 2 will be referred to as a second decomposing unit, a second diffusion filter unit, a second adjusting unit, and a second reconstructing unit; and the functional units on level 3 will be referred to as a third decomposing unit, a third diffusion filter unit, a third adjusting unit, and a third reconstructing unit.

Each of the decomposing units decomposes strain data, by performing a multi-resolution analysis thereon, into low-range decomposed image data and high-range decomposed image data. More specifically, by performing a wavelet transformation process (a discrete wavelet transformation process), each of the decomposing units decomposes the strain data into low-range decomposed image data "LL" and high-range decomposed image data "HL, LH, and HH". In this situation, "LL" is image data in which the components in both the horizontal direction and the vertical direction are low-frequency components. "HL" is image data in which the component in the horizontal direction is a high-frequency component, whereas the component in the vertical direction is a low-frequency component. "LH" is image data in which the component in the horizontal direction is a low-frequency component, whereas the component in the vertical direction is a high-frequency component. "HH" is image data in which the components in both the horizontal direction and the vertical direction are high-frequency components.

Further, each of the decomposing units outputs the "LL" to the decomposing unit positioned on the immediately lower level and outputs the "HL, LH, and HH" to the adjusting unit positioned on the same level. For example, as illustrated in FIG. 2, the first decomposing unit outputs "LL (1st)", which is LL on level 1, to the second decomposing unit and outputs "HL (1st), LH (1st), and HH (1st)", which are HL, LH, and HH on level 1, to the first adjusting unit. Similarly, the second decomposing unit outputs "LL (2nd)", which is LL on level 2, to the third decomposing unit and outputs "HL (2nd), LH (2nd), and HH (2nd)", which are HL, LH, and HH on level 2, to the second adjusting unit.

The decomposing unit positioned on the lowest level outputs the "LL" to the diffusion filter unit positioned on the same level. For example, as illustrated in FIG. 2, the third decomposing unit outputs "LL (3rd)", which is LL on level 3, to the third diffusion filter unit.

After that, each of the diffusion filter units applies a non-linear anisotropic diffusion filter to the "LL". Subsequently, each of the diffusion filter units outputs the "filter-processed LL" to a corresponding one of the reconstructing units. In addition, each of the diffusion filter units detects edge information and outputs the detected edge information to a corresponding one of the adjusting units.

Figure 3:
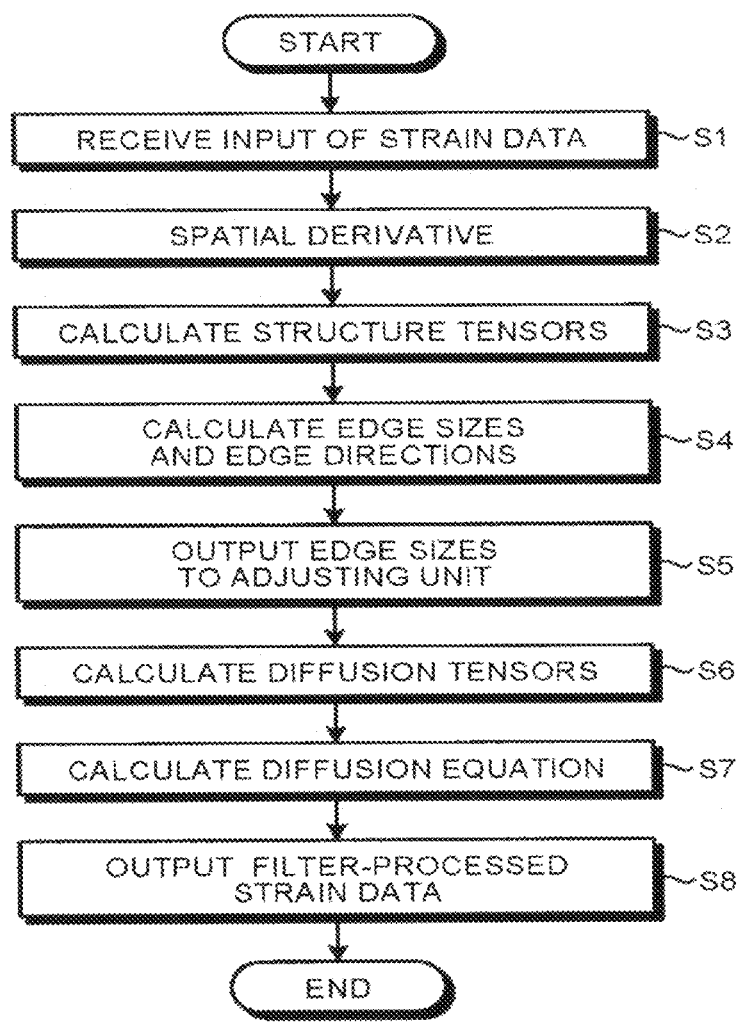
FIG. 3 is a flowchart of a processing procedure performed by each of diffusion filter units according to the conventional method.

FIG. 3 is a flowchart of a processing procedure performed by each of the diffusion filter units according to the conventional method. As illustrated in FIG. 3, the diffusion filter unit receives an input of strain data (step S1). After that, the diffusion filter unit performs a spatial derivative calculation by using the strain data (step S2) so as to obtain structure tensors (step S3). Further, from the structure tensors, the diffusion filter unit calculates edge sizes and edge directions as information (edge information) about the edges in the strain data (step S4). Of the calculated edge information, the diffusion filter unit outputs the edge sizes to the adjusting unit (step S5). Subsequently, the diffusion filter unit calculates diffusion tensors from the edge information (step S6) and calculates a diffusion equation with respect to the strain data, by using the calculated diffusion tensors (step S7). After that, the diffusion filter unit outputs the filter-processed strain data to a corresponding one of the reconstructing units (step S8).

Returning to the description of FIG. 2, each of the adjusting units adjusts signal levels of "HL, LH, and HH", by using the edge information detected by the diffusion filter unit positioned on the same level. After that, each of the adjusting units outputs the "adjusted HL, adjusted LH, and adjusted HH" to the reconstructing unit positioned on the same level. For example, as illustrated in FIG. 2, the third adjusting unit adjusts signal levels of "HL (3rd), LH (3rd), and HH (3rd)" by using the edge information detected by the third diffusion filter unit. After that, as illustrated in FIG. 2, the third adjusting unit outputs the "adjusted HL (3rd), adjusted LH (3rd), and adjusted HH (3rd)" to the third reconstructing unit.

Each of the reconstructing units performs a reconstructing process on the "filter-processed LL" and the "adjusted HL, adjusted LH, and adjusted HH" by performing a multi-resolution synthesizing process. More specifically, each of the reconstructing units synthesizes the "filter-processed LL" with the "adjusted HL, adjusted LH, and adjusted HH" by performing a wavelet inverse transformation process. After that, each of the reconstructing units outputs "output data", which is the data resulting from the reconstructing process, to the diffusion filter unit positioned on the higher level. The reconstructing unit positioned on the highest level outputs the output data to the image generating unit 17.

For example, as illustrated in FIG. 2, the third reconstructing unit synthesizes the "filter-processed LL (3rd)" with the "adjusted HL (3rd), adjusted LH (3rd), and adjusted HH (3rd)". After that, as illustrated in FIG. 2, the third reconstructing unit outputs "level 3 output data", which is the data resulting from the reconstructing process, to the second diffusion filter unit positioned on level 2. Further, as illustrated in FIG. 2, the first reconstructing unit synthesizes the "filter-processed LL (1st)" with the "adjusted HL (1st), adjusted LH (1st), and adjusted HH (1st)". After that, as illustrated in FIG. 2, the first reconstructing unit outputs "level 1 output data", which is the data resulting from the reconstructing process, to the image generating unit 17.

Figure 4:
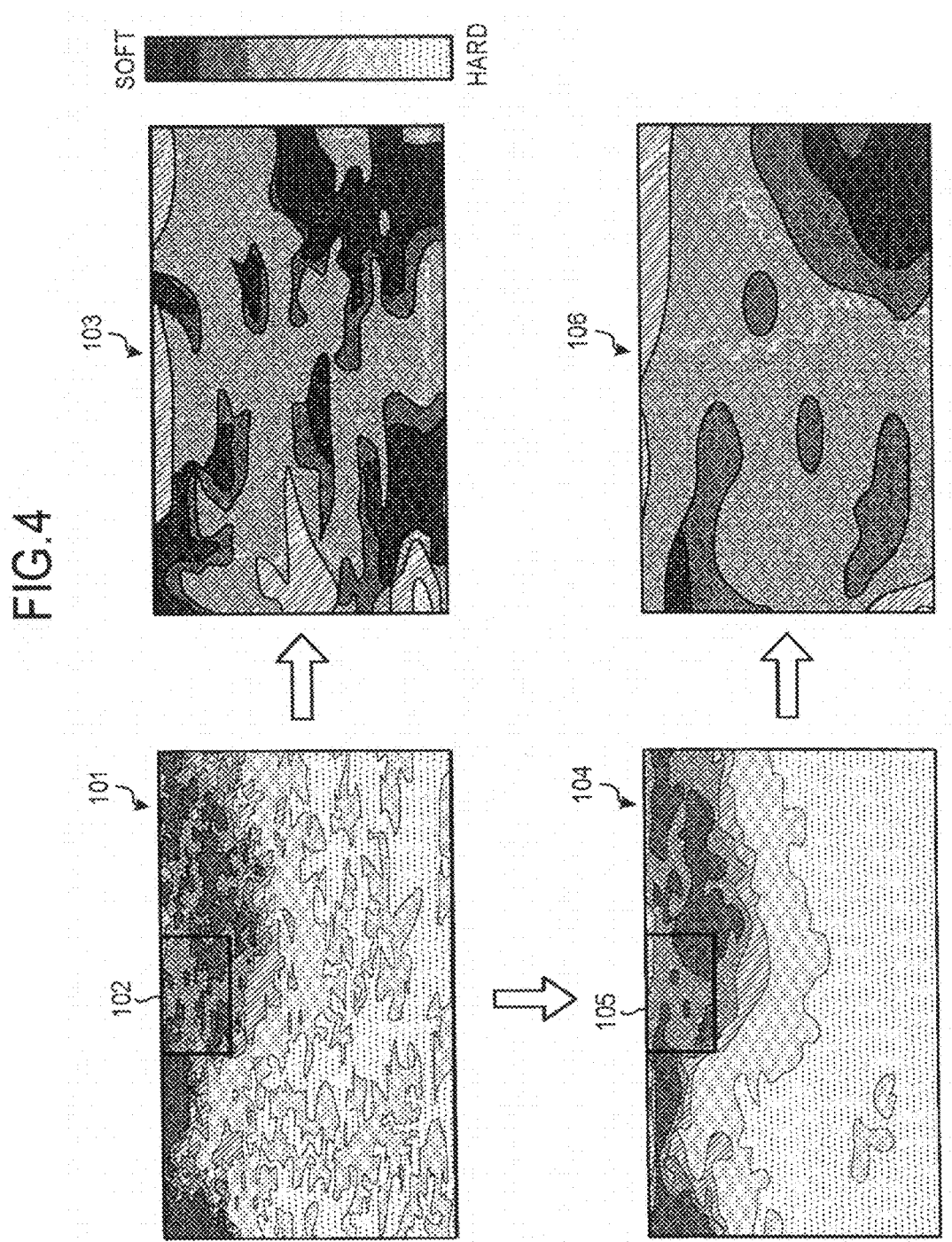
FIG. 4 is a drawing for explaining an image processing unit according to the conventional method.

As explained above, the image processing unit according to the conventional method calculates feature amounts from the strain data itself, which is the target of the filtering process, and performs the filtering process on the strain data on the basis of the calculated feature amounts. FIG. 4 is a drawing for explaining the image processing unit according to the conventional method. FIG. 4 illustrates a strain image 101 generated without performing a filtering process on strain image data and a strain image 104 generated after performing a filtering process. Further, FIG. 4 also illustrates an enlarged view 103 obtained by enlarging a rectangular area 102 in the strain image 101 and an enlarged view 106 obtained by enlarging a rectangular area 105 in the strain image 104. The images illustrated in FIG. 4 are examples of strain images obtained by taking images of a mammary gland.

As illustrated in FIG. 4, the strain image 101 and the strain image 104 are generated as images in which the degrees of hardness of the tissue in the subject's body are expressed in different colors. In the examples illustrated in FIG. 4, for the sake of convenience in the explanation, the images are rendered in such a manner that the harder the tissue at the site in the subject's body is, the closer to white the color is, and the softer the tissue at the site in the subject's body is, the closer to black the color is. The harder sites indicated in the strain image 101 have been smoothed in the strain image 104 resulting from the filtering process.

In contrast, the softer sites indicated in the strain image 101 are not smoothed so as to maintain the tissue structure in the strain image 104 resulting from the filtering process. More specifically, as the enlarged view 103 is compared with the enlarged view 106, some of the strain values in the softer sites in the enlarged view 106 are decreased. In other words, the softer sites are smoothed so as to be generally blurry at the boundary sites where the degrees of hardness vary, so that the tissue structure is not definite.

As explained here, as for the filtering process performed by the image processing unit according to the conventional method, when the filtering process is performed on the strain data, it is not possible to achieve a sufficient level of resolution in the softer sites even with the filtering process, and it is difficult to recognize the relationship with the tissue structure. More specifically, the image processing unit according to the conventional method calculates the feature amounts of the image data from the strain data itself, which is the target of the filtering process. However, because the resolution of the strain data is lower in softer sites, it is difficult to calculate appropriate feature amounts. For this reason, as for the filtering process performed by the image processing unit according to the conventional method, it is not possible to achieve a sufficient effect even if the filtering process is applied to the strain data.

To cope with this situation, the image processing unit 16 according to the first embodiment, for example, calculates feature amounts from the B-mode data and corrects the strain data on the basis of the calculated feature amounts. In other words, the image processing unit 16 according to the first embodiment calculates the feature amounts from at least such a part of second image data that overlaps with first image data, the second image data having an image taking region of which at least a part overlaps with that of the first image data and using a parameter that is different from that of the first image data as an imaged target and corrects such a part of the first image data that overlaps with the second image data on the basis of the calculated feature amounts.

It should be noted that, when the elastography mode is specified, the B-mode data generating process performed by the B-mode processing unit 13 and the strain data generating process performed by the strain data processing unit 15 are performed in a time-divided manner in the first embodiment.

Figure 5:
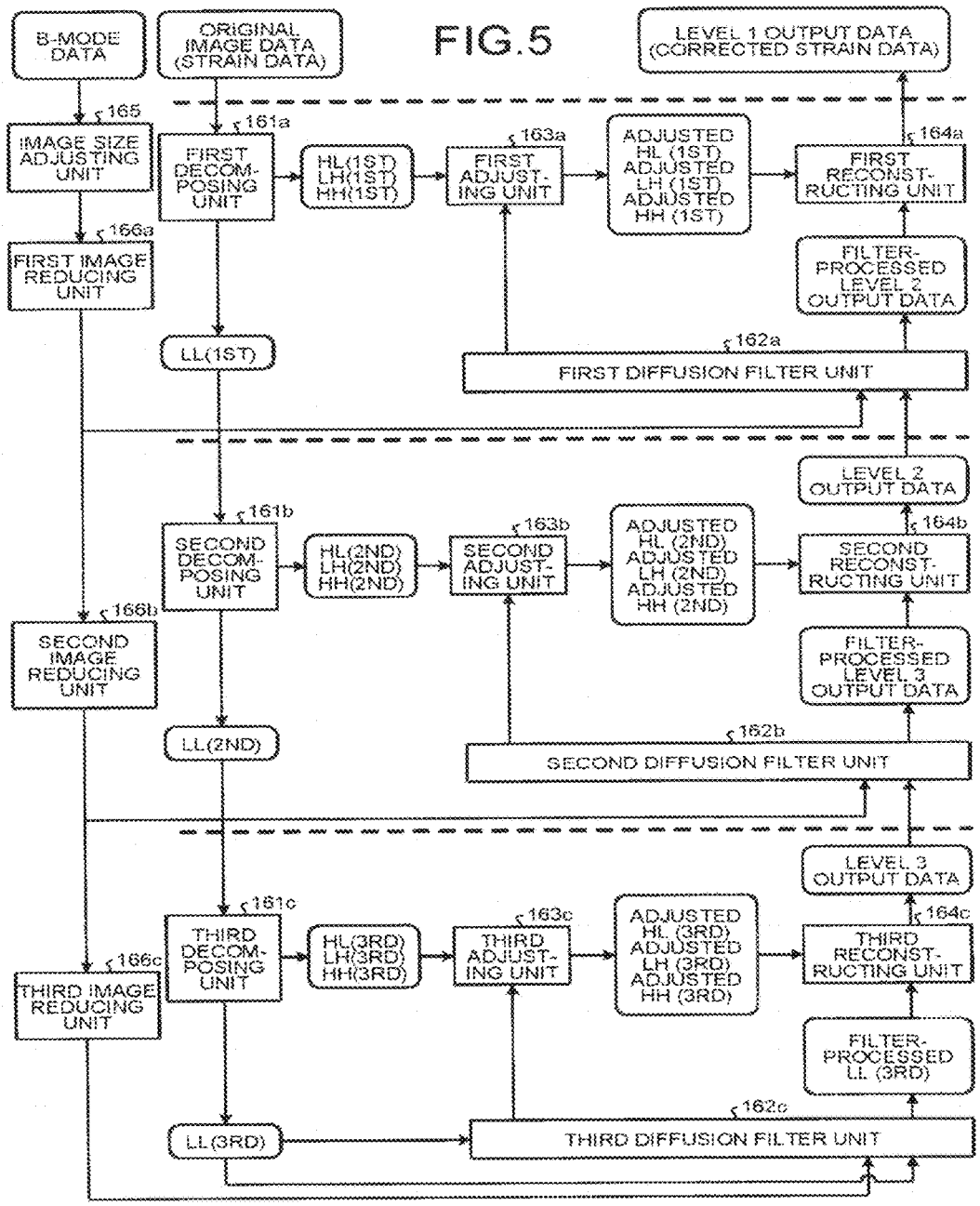
FIG. 5 is a block diagram of a configuration of an image processing unit according to the first embodiment.

FIG. 5 is a functional block diagram of a configuration of the image processing unit 16 according to the first embodiment. As illustrated in FIG. 5, the image processing unit 16 according to the first embodiment includes a decomposing unit 161, a diffusion filter unit 162, an adjusting unit 163, a reconstructing unit 164, and an image reducing unit 166 on each of the levels. For the sake of convenience in the explanation, when it is necessary to distinguish the decomposing units 161, the diffusion filter units 162, the adjusting units 163, the reconstructing units 164, and the image reducing units 166 on the different levels from one another, the functional units may be referred to as follows: The functional units on level 1 will be referred to as a first decomposing unit 161a, a first diffusion filter unit 162a, a first adjusting unit 163a, a first reconstructing unit 164a, and a first image reducing unit 166a; the functional units on level 2 will be referred to as a second decomposing unit 161b, a second diffusion filter unit 162b, a second adjusting unit 163b, a second reconstructing unit 164b, and a second image reducing unit 166b; and the functional units on level 3 will be referred to as a third decomposing unit 161c, a third diffusion filter unit 162c, a third adjusting unit 163c, a third reconstructing unit 164c, and a third image reducing unit 166c. Further, an image size adjusting unit 165 is provided on the highest level. In other words, the image size adjusting unit 165 is provided on level 1.

The image size adjusting unit 165 cuts out an area having the same spatial region with the strain data from the B-mode data and adjusts the size of the B-mode data so that the pixel size thereof becomes the same as that of the strain data. In this situation, it is sufficient if the image size adjusting unit 165 arranges the pixel size of the strain data to be the same as the pixel size of the B-mode data, in preparation for the processes performed at the subsequent stages. Thus, the image size adjusting unit 165 may change only the size of the strain data or may change both the size of the strain data and the size of the B-mode data.

Each of the decomposing units 161 decomposes strain data, by performing a multi-resolution analysis thereon, into low-range decomposed image data and high-range decomposed image data. More specifically, by performing a wavelet transformation process (a discrete wavelet transformation process), each of the decomposing units 161 decomposes the strain data into low-range decomposed image data "LL" and high-range decomposed image data "HL, LH, and HH". In this situation, "LL" is image data in which the components in both the horizontal direction and the vertical direction are low-frequency components. "HL" is image data in which the component in the horizontal direction is a high-frequency component, whereas the component in the vertical direction is a low-frequency component. "LH" is image data in which the component in the horizontal direction is a low-frequency component, whereas the component in the vertical direction is a high-frequency component. "HH" is image data in which the components in both the horizontal direction and the vertical direction are high-frequency components.

Further, each of the decomposing units 161 outputs the "LL" to the decomposing unit 161 positioned on the immediately lower level and outputs the "HL, LH, and HH" to the adjusting unit 163 positioned on the same level. For example, as illustrated in FIG. 5, the first decomposing unit 161*a* outputs "LL (1st)", which is LL on level 1, to the second decomposing unit 161*b* and outputs "HL (1st), LH (1st), and HH (1st)", which are HL, LH, and HH on level 1, to the first adjusting unit 163*a*. Similarly, the second decomposing unit 161*b* outputs "LL (2nd)", which is LL on level 2, to the third decomposing unit 161*c* and outputs "HL (2nd), LH (2nd), and HH (2nd)", which are HL, LH, and HH on level 2, to the second adjusting unit 163*b*.

The decomposing unit 161 positioned on the lowest level outputs the "LL" to the diffusion filter unit 162 positioned on the same level. For example, as illustrated in FIG. 5, the third decomposing unit 161*c* outputs "LL (3rd)", which is LL on level 3, to the third diffusion filter unit 162*c*.

Each of the image reducing units 166 reduces the image size of B-mode data received as an input, so as to be the same as the image size of the low-range decomposed image data "LL" of the strain data decomposed by a corresponding one of the decomposing units 161. In other words, each of the image reducing units 166 reduces the image size of the B-mode data so as to be the same as the image size of the image data generated by the decomposing unit 161 positioned on the same level. After that, each of the image reducing units 166 outputs the reduced B-mode data to the diffusion filter unit 162 positioned on the same level and to the image reducing unit 166 positioned on the immediately lower level. In this situation, the image reducing unit 166 positioned on the lowest level outputs the reduced B-mode data only to the diffusion filter unit 162 positioned on the same level. Filter coefficients used for the reduction of the images can be used in common as low-range filters used by the decomposing units 161.

Each of the diffusion filter units 162 calculates edge directions and edge sizes in the B-mode data as feature amounts, from the B-mode data reduced by a corresponding one of the image reducing units 166, and smooths the low-range decomposed image data "LL" of the strain data decomposed by a corresponding one of the decomposing units 161 on the basis of the calculated feature amounts. In other words, each of the diffusion filter units 162 calculates the edge sizes and the edge directions of the B-mode data as the feature amounts, from at least such a part of the reduced B-mode data on the level that overlaps with the low-range decomposed image data "LL" and further smooths, along the edge directions, such a part of the low-range strain data resulting from the multi-resolution decomposition on the level that overlaps with the reduced B-mode data, on the basis of the edge sizes. For example, each of the diffusion filter units 162 applies a non-linear anisotropic diffusion filter to the "LL". After that, each of the diffusion filter units 162 outputs the "filter-processed LL" to a corresponding one of the reconstructing units 164. In addition, each of the diffusion filter units 162 detects the edge information (the edge sizes) and outputs the detected edge information to a corresponding one of the adjusting units 163.

Each of the adjusting units 163 adjusts signal levels of the "HL, LL, and HH", by using the edge information detected by the diffusion filter unit 162 positioned on the same level. For example, each of the adjusting units 163 reduces noise by eliminating signals smaller than the edge sizes calculated by a corresponding one of the diffusion filter units 162 as the noise, from the high-range decomposed image data "HL, LH, and HH" of the strain data decomposed by a corresponding one of the decomposing units 161. After that, each of the adjusting units 163 outputs the "adjusted HL, adjusted LH, and adjusted HH" to the reconstructing unit 164 positioned on the same level. For example, as illustrated in FIG. 5, the third adjusting unit 163*c* adjusts signal levels of "HL (3rd), LH (3rd), and HH (3rd)" by using the edge information detected by the third diffusion filter unit 162*c*. After that, as illustrated in FIG. 5, the third adjusting unit 163*c* outputs the "adjusted HL (3rd), adjusted LH (3rd), and adjusted HH (3rd)" to the third reconstructing unit 164*c*.

Each of the reconstructing units 164 generates new strain data by synthesizing the high-range decomposed image data "HL, LH, and HH" of the strain data from which the noise was eliminated by a corresponding one of the adjusting units 163 with the low-range decomposed image data "LL" of the strain data that was smoothed by a corresponding one of the diffusion filter units 162. In other words, each of the reconstructing units 164 generates corrected strain data by performing a reconstructing process on the "filter-processed LL" and the "adjusted HL, adjusted LH, and adjusted HH", through a multi-resolution synthesizing process. More specifically, each of the reconstructing units 164 synthesizes the "filter-processed LL" with the "adjusted HL, adjusted LH, and adjusted HH" by performing a wavelet inverse transformation process. After that, each of the reconstructing units 164 outputs "output data", which is the data resulting from the reconstructing process, to the diffusion filter unit 162 positioned on the higher level. The reconstructing unit 164 positioned en the highest level outputs the output data to the image generating unit 17.

For example, as illustrated in FIG. 5, the third reconstructing unit 164*c* synthesizes the "filter-processed LL (3rd)" with the "adjusted HL (3rd), adjusted LH (3rd), and adjusted HH (3rd)". After that, as illustrated in FIG. 5, the third reconstructing unit 164*c* outputs "level 3 output data", which is the data resulting from the reconstructing process, to the second diffusion filter unit 162*b* positioned on level 2. Further, as illustrated in FIG. 5, the first reconstructing unit 164*a* synthesizes the "filter-processed LL (1st)" with the "adjusted HL (1st), adjusted LH (1st), and adjusted HH (1st)". After that, as illustrated in FIG. 5, the first reconstructing unit 164*a* outputs "level 1 output data", which is the data resulting from the reconstructing process, to the image generating unit 17. In this situation, the wavelet transformation process and the wavelet inverse transformation process are examples of multi-resolution analyses. It is acceptable to apply any other multi-resolution analyzing method such as a Laplacian pyramid method.

Figure 6:
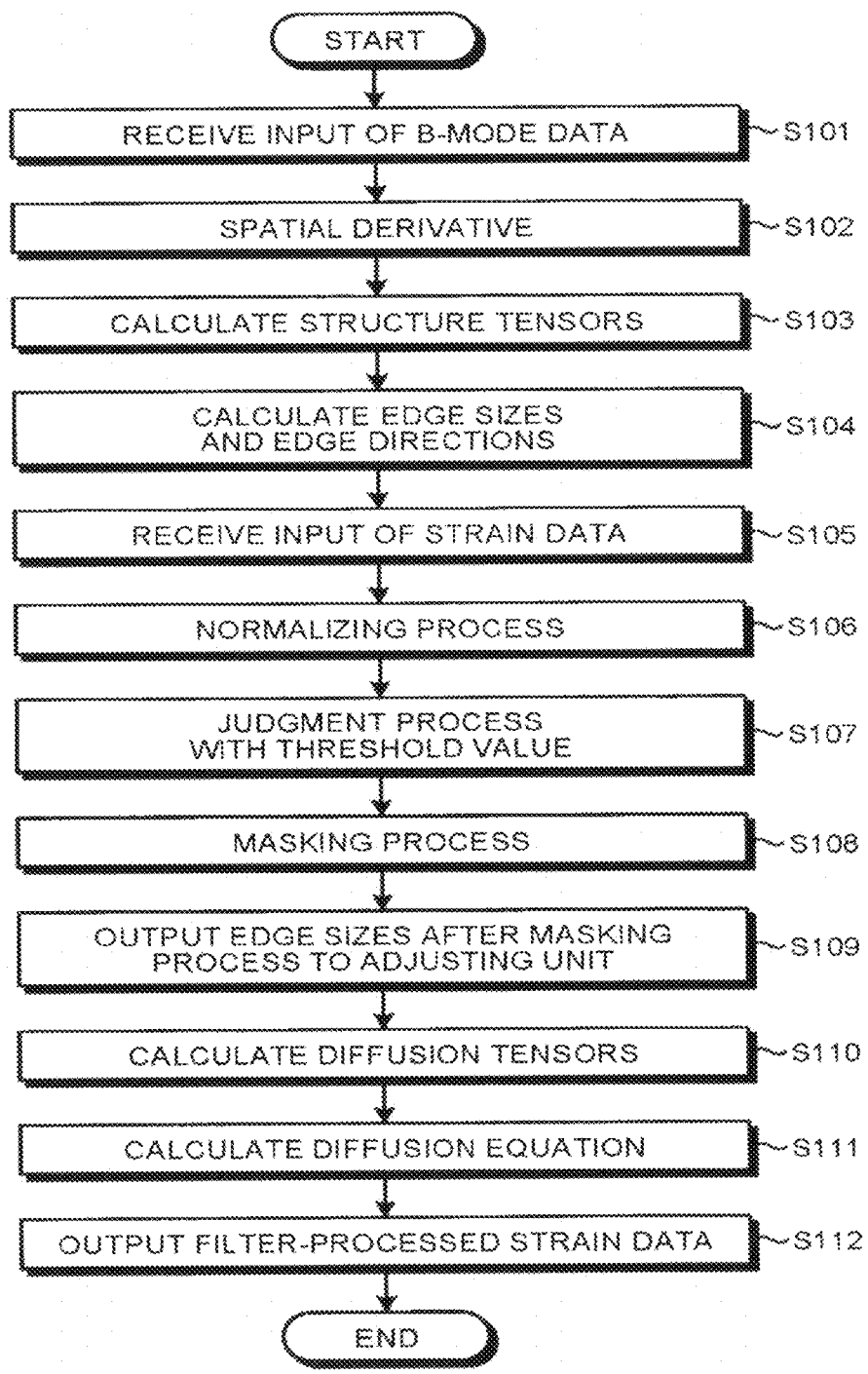
FIG. 6 is a flowchart of a processing procedure performed by each of diffusion filter units according to the first embodiment.

Next, a processing procedure performed by each of the diffusion filter units 162 will be explained. FIG. 6 is a flowchart of the processing procedure performed by each of the diffusion filter units 162 according to the first embodiment. As illustrated in FIG. 6, the diffusion filter unit 162 receives an input of B-mode data (step S101). After that, the diffusion filter unit 162 performs a spatial derivative calculation on the pixel levels (brightness values) of the B-mode data in the horizontal direction (the widthwise direction or the x direction) and the vertical direction (the lengthwise direction or the y direction) (step S102) so as to obtain structure tensors (step S103). In this situation, the structure tensors are tensors calculated for the purpose of detecting edge sizes and edge directions. The eigenvalue of a structure tensor is associated with the edge size, whereas the eigenvector of a structure tensor expresses the edge direction. A structure tensor "S" can be defined as indicated in Expression (1) below:

$$S = G_\rho * \begin{pmatrix} I_x^2 & I_x I_y \\ I_x I_y & I_y^2 \end{pmatrix} = \begin{pmatrix} G_\rho * I_x^2 & G_\rho * (I_x I_y) \\ G_\rho * (I_x I_y) & G_\rho * I_y^2 \end{pmatrix} = \begin{pmatrix} s_{11} & s_{12} \\ s_{12} & s_{22} \end{pmatrix} \quad (1)$$

In Expression (1), "$I_x$" is a spatial derivative in the x-direction of a pixel level "I" of the input image data. In Expression (1), "$I_y$" is a spatial derivative in the y direction of "I". Further, "$G_\rho$" denotes a two-dimensional Gaussian function, whereas the operator "*" denotes a convolution. For example, the third diffusion filter unit 162c differentiates "LL (3rd)" in the horizontal direction (the widthwise direction or the x direction) and the vertical direction (the lengthwise direction or the y direction) and calculates a structure tensor "$s_{11}, s_{12}, s_{22}$" indicated in Expression (1).

The calculation of the structure tensors does not necessarily have to strictly follow the method described above. It is acceptable to apply a sobel filter, instead of calculating "$I_x$" and "$I_y$" at the first stage of the process.

After that, the diffusion filter unit 162 calculates the edge sizes and the edge directions as information (edge information) about the edges in the B-mode data, from elements of the calculated structure tensors (step S104).

Further, the diffusion filter unit 162 smooths the strain data along the edge directions, on the basis of the edge sizes calculated from the B-mode data with respect to softer sites that are selected from between harder sites and the softer sites within the strain data. For example, the diffusion filter unit 162 receives an input of the strain data (step S105) and normalizes strain values of the pixels in the strain data (step S106). For example, the diffusion filter unit 162 normalizes the strains values of the pixels with an average value or a maximum value. After that, the diffusion filter unit 162 judges the normalized strain values with a threshold value (step S107). For example, if the normalized strain value of a pixel is smaller than the threshold value, the diffusion filter unit 162 considers the strain value to be a true value. Subsequently, the diffusion filter unit 162 performs a masking process on the basis of the result of the threshold judgment process (step S108). For example, if the normalized strain value of a pixel is smaller than the threshold value, the diffusion filter unit 162 determines the edge size to be "0". As a result, the diffusion filter unit 162 performs the processes thereafter, while considering the harder sites as sites having no edges. On the contrary, if the normalized strain value of a pixel is equal to or larger than the threshold value, the diffusion filter unit 162 uses the edge size detected at step S104 as the edge size thereof. As a result, the diffusion filter unit 162 performs the processes thereafter, while considering the edge sizes of the softer sites to be the edge sizes calculated from the B-mode data. Further, the diffusion filter unit 162 outputs the edge sizes after the masking process to the adjusting unit 163 (step S109).

Subsequently, the diffusion filter unit 162 calculates diffusion tensors (step S110). A diffusion tensor "D" is defined as indicated in Expression (2) below:

$$D = \begin{pmatrix} d_{11} & d_{12} \\ d_{12} & d_{22} \end{pmatrix} = R \begin{pmatrix} \lambda_1 & 0 \\ 0 & \lambda_2 \end{pmatrix} R^T \quad (2)$$

In Expression (2), "R" denotes a reaction matrix, whereas "$R^T$" denotes a transposed matrix of "R". Further, "$\lambda_1, \lambda_2$" in Expression (2) are diffusion filter coefficients calculated on the basis of the edge information. For example, by using Expression (2), the third diffusion filter unit 162c calculates a diffusion tensor "$d_{11}, d_{12}$, and $d_{22}$" for "LL (3rd)".

After that, the diffusion filter unit 162 calculates a diffusion equation with respect to the strain data (step S111). A non-linear anisotropic diffusion filter can be expressed by using Expression (3) below that is a partial differential equation.

$$\frac{\partial I}{\partial t} = div[D\nabla I] \quad (3)$$

"$\nabla I$ (nabla I)" in Expression (3) denotes a gradient vector of "I", whereas "t" in Expression (3) denotes a time related to the processing. Further, "div" in Expression (3) denotes a divergence.

In other words, the calculating process "$D\nabla I$" performed by the diffusion filter unit 162 while using Expression (3) is a calculating process to multiply a specific direction with respect to the gradient vector of each of the pixels and a direction perpendicular to the specific direction by "$\lambda_1$" and "$\lambda_2$". In this situation, the specific direction is the edge direction of the image data. The diffusion filter coefficients are calculated in accordance with the edge sizes.

After that, the diffusion filter unit 162 performs a non-linear anisotropic diffusion filtering process by performing a numerical value analytical calculation using the partial differential equation of Expression (3) one time or a plurality of times repeatedly. For example, by using pixel levels of a pixel at a point and at multiple points (e.g., nine points) in the surroundings of the pixel at t time "t" as well as the element values of the diffusion tensor, the diffusion filter unit 162 calculates new pixel levels at the points at a time "t+Δt" and further performs the same calculation by using "t+Δt" as a new "t" either one time or a plurality of times repeatedly. For example, the third diffusion filter unit 162c performs the non-linear anisotropic diffusion filtering process on "LL (3rd)" and "HL (3rd), LH (3rd), and HH (3rd)". Thus, for a site having an edge, the diffusion filter unit 162 performs the smoothing process along the edge direction, but does not perform the smoothing process in the direction perpendicular to the edge. In contrast, for a site having no edge, the diffusion filter unit 162 performs the smoothing process regardless of the edge direction. By changing the degree of the smoothing process in this manner according to whether the tissue has edges or not and the directions thereof, the diffusion filter unit 162 is able to reduce the noise without sacrificing the resolution.

As for the method for calculating "$\lambda_1, \lambda_2$", it is desirable to prepare a general mathematical formula and to make adjustments by using a number of parameters, so that it is possible to make changes according to characteristics of ultrasound images in various diagnosis fields.

After that, the diffusion filter unit 162 outputs the filter-processed strain data to a corresponding one of the reconstructing units 164 (step S112).

Figure 7:
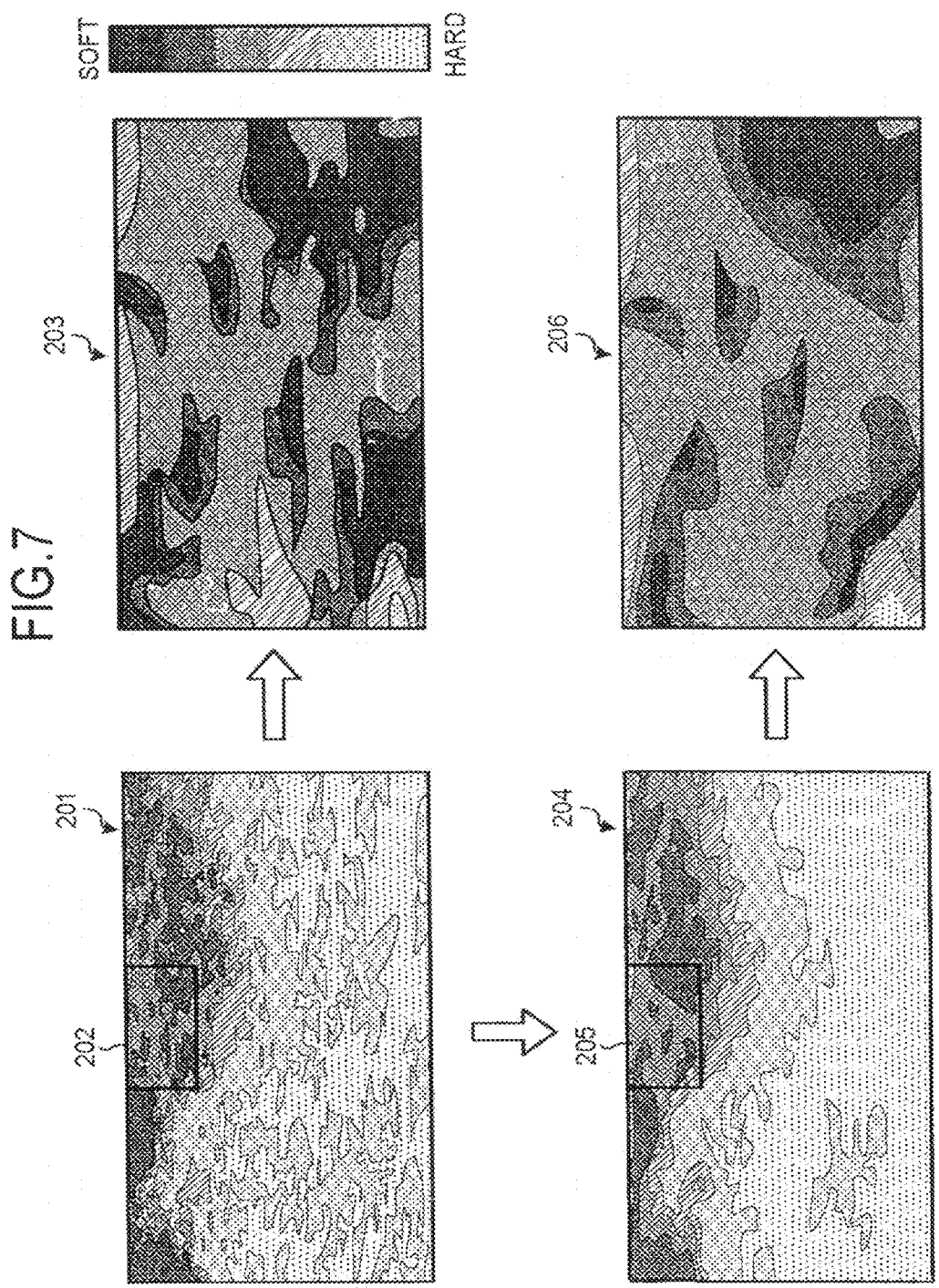
FIG. 7 is a drawing for explaining the image processing unit according to the first embodiment.

FIG. 7 is a drawing for explaining the image processing unit 16 according to the first embodiment. FIG. 7 illustrates a strain image 201 generated without performing a filtering process on strain image data and a strain image 204 generated after performing a filtering process. Further, FIG. 7 also illustrates an enlarged view 203 obtained by enlarging a rectangular area 202 in the strain image 201 and an enlarged view 206 obtained by enlarging a rectangular area 205 in the strain image 204. The images illustrated in FIG. 7 are examples of strain images obtained by taking images of mammary gland.

As illustrated in FIG. 7, the strain image 201 and the strain image 204 are generated as images in which the degrees of hardness of the tissue in the subject's body are expressed in different colors. In the examples illustrated in FIG. 7, for the sake of convenience in the explanation, the images are rendered in such a manner that the harder the tissue at the site in the subject's body is, the closer to white the color is, and the softer the tissue at the site in the subject's body is, the closer to black the color is. The harder sites indicated in the strain image 201 have been smoothed in the strain image 204 resulting from the filtering process.

In contrast, the softer sites indicated in the strain image 201 have been smoothed while maintaining the tissue structure in the strain image 204 resulting from the filtering process. More specifically, as the enlarged view 203 is compared with the enlarged view 206, the decreases in the strain values in the softer sites in the enlarged view 206 are smaller. Further, as the enlarged view 206 is compared with the enlarged view 106 in FIG. 4, the softer sites in the enlarged view 206 have been smoothed while the boundary sites where the degrees of hardness vary are maintained, so that the tissue structure is more definite than that in the enlarged view 106.

After that, the image generating unit 17 generates an elastography image by generating a strain image from the strain data on which the filtering process was performed by the image processing unit 16 and superimposing the generated strain image on the B-mode image.

Figure 8:
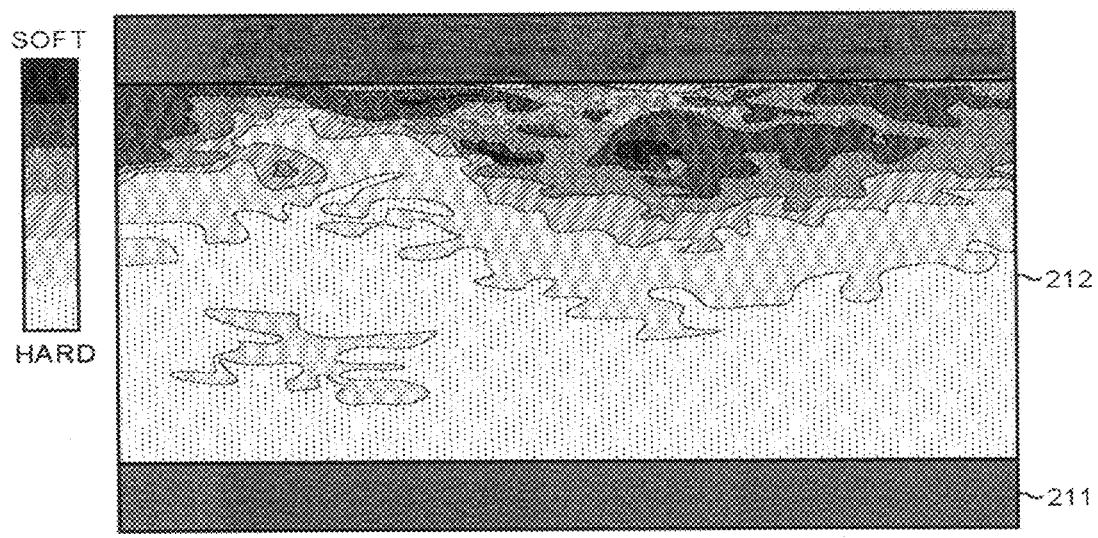
FIG. 8 is a drawing for explaining an image generating unit according to the first embodiment.

FIG. 8 is a drawing for explaining the image generating unit 17 according to the first embodiment. FIG. 8 illustrates an elastography image generated after the filtering process performed by the image processing unit 16 according to the first embodiment. As illustrated in FIG. 8, the image generating unit 17 generates an elastography image by superimposing a strain image 212 on a B-mode image 211. In the elastography image generated by the image generating unit 17 in this manner, the tissue structure of the softer sites is maintained, and the relationship with the B-mode image is definite.

As explained above, according to the first embodiment, the edge sizes and the edge directions are calculated from the B-mode data as the feature amounts, and the calculated feature amounts are used as the feature amounts of the non-linear anisotropic diffusion filter. In this situation, because the tissue structure is definite in the B-mode data, it is possible to calculate the appropriate feature amounts. As a result, according to the first embodiment, because the feature amounts calculated from the B-mode data are used as the feature amounts of the non-linear anisotropic diffusion filter, it is possible to obtain the feature amounts that are more appropriate than in the situation where feature amounts are obtained from the strain data itself, which is the target of the filtering process. As a result, even if the filtering process is performed on the softer sites in the strain data, because the smoothing process is performed according to the edge sizes and the edge directions, it is possible to make the relationship between the strains and the tissue structure definite.

Further, when an anisotropic diffusion filter is applied to harder sites by using the edge information of the B-mode data, there is a tendency that patterns following the edge directions in the B-mode image are rendered with an unnaturally high intensity. To cope with this situation, according to the first embodiment, each of the diffusion filter units 162 excludes the harder sites from the target of the filtering process. For example, each of the diffusion filter units 162 normalizes the strain values of the pixels in the strain data, performs the threshold judgment process on the normalized values, and performs the masking process on the basis of the result of the threshold judgment process (the processes at steps S104 through S106 in FIG. 6). As a result, by treating the harder sites (i.e., the sites having smaller strains) as sites having no edge, the diffusion filter units 162 reduce the rendering of the unnatural patterns. The diffusion filter units 162 may omit the processes at steps S104 through S106 illustrated in FIG. 6. Alternatively, in place of the processes at steps S104 through S106 illustrated in FIG. 6, the ultrasound diagnosis apparatus may receive a selection of a region that serves as a target of the filtering process from the operator. In that situation, the image processing unit 16 receives the selection of a rectangular region, a circular region, or an arbitrary region from the operator via the input device 3 and performs the filtering process only on the pixels within the received region.

Second Embodiment

In the first embodiment, the example is explained in which the strain data processing unit 15 generates the strain data from the reflected-wave data. The strain data, however, may be generated from velocity components of tissue Doppler data. Further, the Doppler processing unit 14 is capable of generating tissue Doppler data by implementing a tissue Doppler method. For this reason, in a second embodiment, an example will be explained in which a strain data processing unit generates strain data from the velocity components of tissue Doppler data. Further, in the second embodiment, an example will be explained in which the image processing unit 16 calculates feature amounts from power values of the tissue Doppler data.

Figure 9:
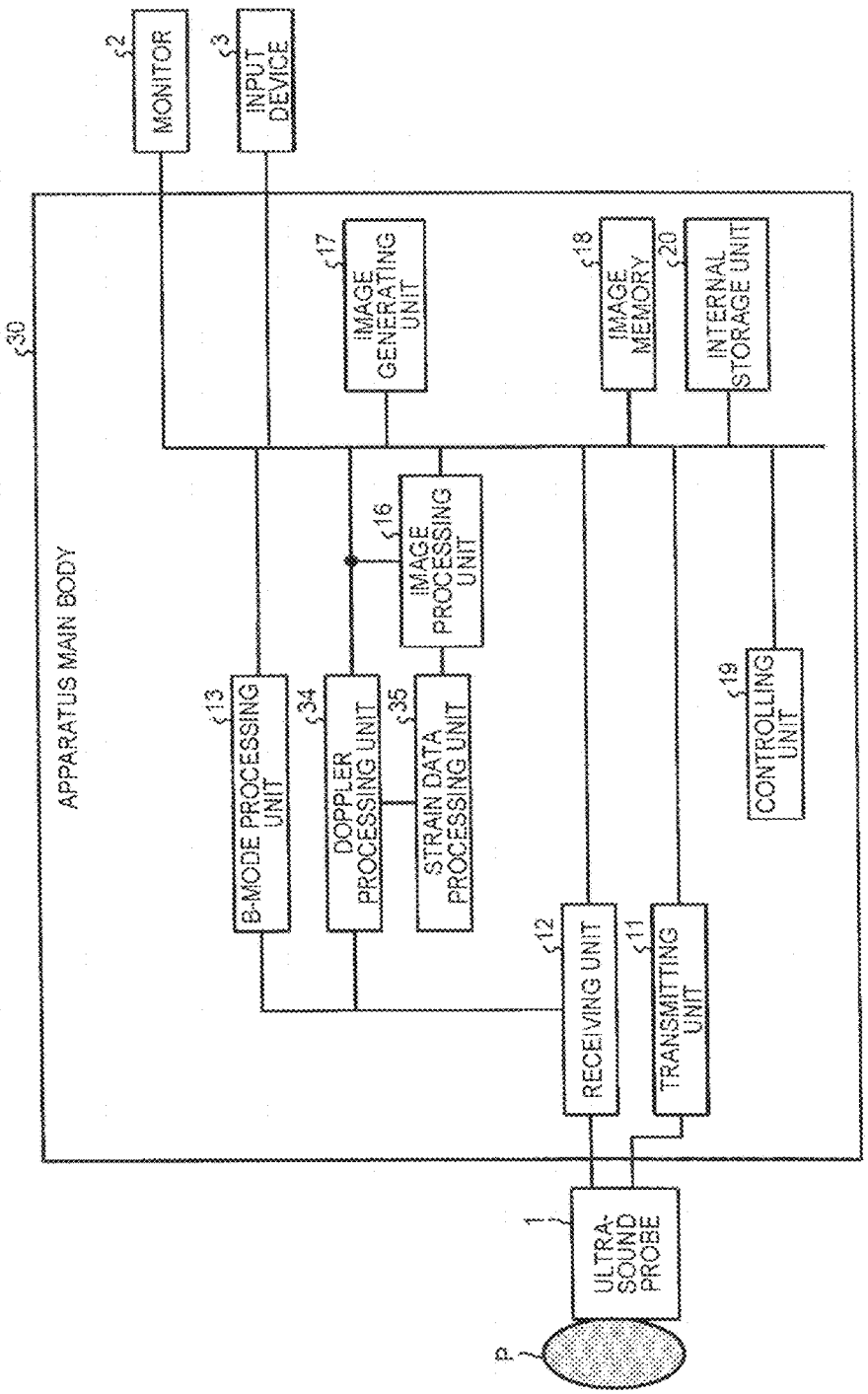
FIG. 9 is a drawing for explaining an overall configuration of an ultrasound diagnosis apparatus according to a second embodiment.

FIG. 9 is a drawing for explaining an overall configuration of an ultrasound diagnosis apparatus according to the second embodiment. As illustrated in FIG. 9, the ultrasound diagnosis apparatus according to the second embodiment includes the ultrasound probe 1, the monitor 2, the input device 3, and an apparatus main body 30. Some of the functional units that play the same roles as those illustrated in FIG. 1 will be referred to by using the same reference characters, and detailed explanation thereof will be omitted.

The apparatus main body 30 is an apparatus that generates an ultrasound image on the basis of the reflected waves received by the ultrasound probe 1. As illustrated in FIG. 9, the apparatus main body 30 includes the transmitting unit 11, the receiving unit 12, the B-mode processing unit 13, a Doppler processing unit 34, a strain data processing unit 35, the image processing unit 16, the image generating unit 17, the image memory 18, the controlling unit 19, and the internal storage unit 20. Some of the functional units that play the same roles as those illustrated in FIG. 1 will be referred to by using the same reference characters, and detailed explanation thereof will be omitted.

When the elastography mode is specified, in the second embodiment, the B-mode data generating process performed by the B-mode processing unit 13 and the Doppler data generating process performed by the Doppler processing unit 34 are performed in a time-divided manner. Of the Doppler data generated by the Doppler processing unit 34, power values of the Doppler data are output to the image processing unit 16, whereas the velocity components of velocity distribution information are output to the strain data processing unit 35.

The Doppler processing unit 34 according to the second embodiment generates data (tissue Doppler data) obtained by extracting movement information on the basis of a Doppler effect on the tissue in the scanned region, by performing a frequency analysis on the reflected-wave data received from the receiving unit 12. More specifically, the Doppler processing unit 34 generates the tissue Doppler data obtained by extracting, as the movement information of the tissue that is a moving member, a velocity, a dispersion value, and a power value, for a plurality of points in a two-dimensional space or a three-dimensional space. After that, when the elastography mode is specified, the Doppler processing unit 34 outputs the velocity components of the tissue Doppler data to the strain data processing unit 35 as the velocity distribution information. Further, when the elastography mode is specified, the Doppler processing unit 34 outputs the power values of the tissue Doppler data to the image processing unit 16. In contrast, if the tissue Doppler mode is specified, the Doppler processing unit 34 outputs the tissue Doppler data to the image generating unit 17.

The strain data processing unit 35 according to the second embodiment generates strain data by calculating strains from the velocity components of the velocity distribution information obtained from the Doppler processing unit 34. For example, the strain data processing unit 35 calculates a displacement by time-integrating the velocity components of the velocity distribution information obtained from the Doppler processing unit 34. Subsequently, the strain data processing unit 35 calculates local strains of the tissue by performing a predetermined calculation (e.g., a spatial derivative) while using the calculated displacement. After that, the strain data processing unit 35 generates the strain data by color-coding and mapping the calculated local strain values of the tissue into corresponding positions.

After that, for example, the image processing unit 16 according to the second embodiment calculates feature amounts from the power values of the tissue Doppler data and corrects the strain data on the basis of the calculated feature amounts. In other words, the image processing unit 16 according to the second embodiment calculates the feature amounts from at least such a part of second image data that overlaps with first image data, the second image data having an image taking region of which at least a part overlaps with that of the first image data and using a parameter that is different from that of the first image data as an imaged target and corrects such a part of the first image data that overlaps with the second image data on the basis of the calculated feature amounts. The configuration of the image processing unit 16 according to the second embodiment is the same as the configuration of the image processing unit 16 according to the first embodiment illustrated in FIG. 5. In the present example, when the image data processed by the image processing unit 16 according to the second embodiment is configured with strain image data and the power values of the Doppler data, the strain image data and the power values of the Doppler data are generated from mutually the same Doppler signals.

Figure 10:
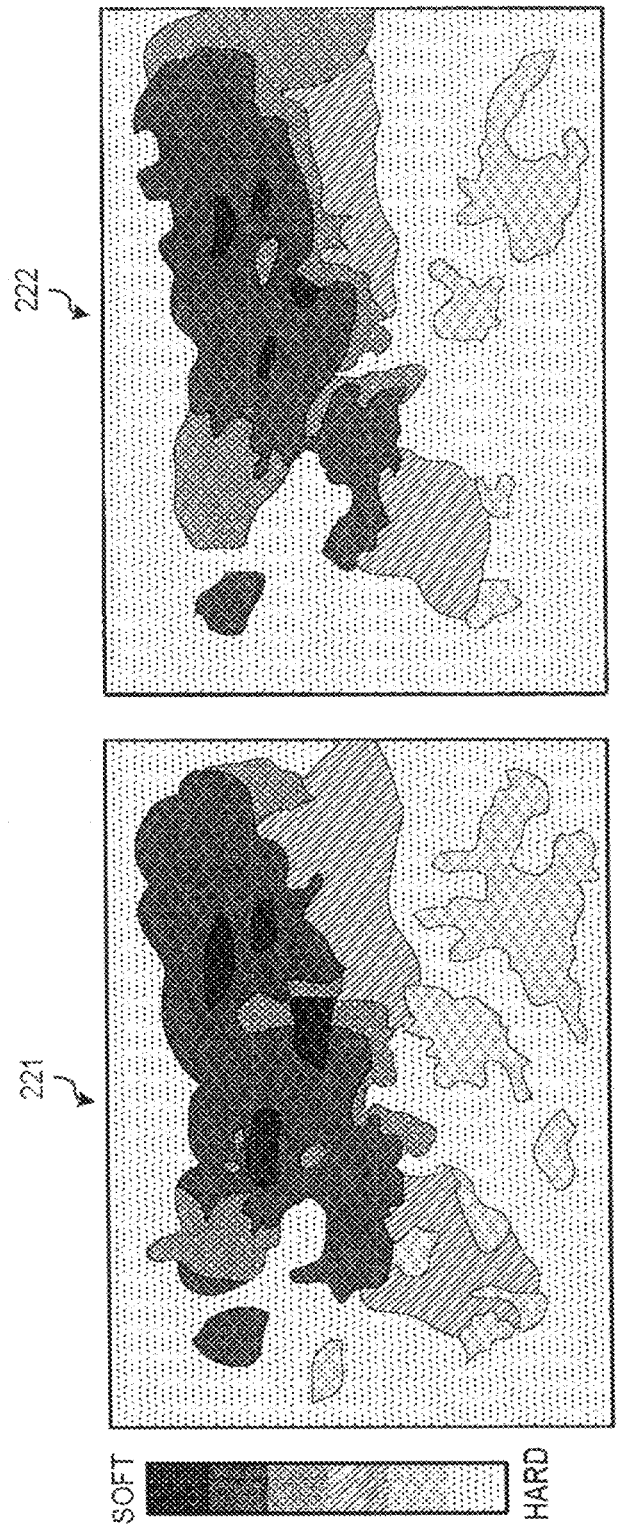
FIG. 10 is a drawing for explaining an image processing unit according to the second embodiment.

FIG. 10 is a drawing for explaining the image processing unit 16 according to the second embodiment. FIG. 10 illustrates a strain image 221 generated without performing a filtering process on strain image data and a strain image 222 generated after performing a filtering process.

As illustrated in FIG. 10, the strain image 221 and the strain image 222 are generated as images in which the degrees of hardness of the tissue in the subject's body are expressed in different colors. In the examples illustrated in FIG. 10, for the sake of convenience in the explanation, the images are rendered in such a manner that the harder the tissue at the site in the subject's body is, the closer to white the color is, and the softer the tissue at the site in the subject's body is, the closer to black the color is. As illustrated in FIG. 10, the harder sites indicated in the strain image 221 have been smoothed in the strain image 222 resulting from the filtering process. In contrast, the softer sites indicated in the strain image 221 maintain the tissue structure at the softer sites in the strain image 222 resulting from the filtering process.

After that, the image generating unit 17 generates an elastography image by generating a strain image from the strain data on which the filtering process was performed by the image processing unit 16 and superimposing the generated strain image on the B-mode image.

As explained above, according to the second embodiment, because the edge sizes and directions are calculated as the feature amounts from the power values of the tissue Doppler data, it is possible to make the relationship between the strain data and the tissue structure more definite than in the situation where the feature amounts are obtained from the strain data itself, which is the target of the filtering process.

Further, according to the second embodiment, the strain image data and the power values of the Doppler image data are generated from mutually the same Doppler signals. As a result, it is possible to reduce the processing load of the apparatus main body 30.

Third Embodiment

In the exemplary embodiments described above, the examples are explained in which the ultrasound diagnosis apparatus performs the processes. However, the image processing processes explained in the exemplary embodiments above may be performed by an image processing apparatus that is provided independently of the ultrasound diagnosis apparatus. More specifically, an image processing apparatus having the functions of the image processing unit 16 illustrated in FIG. 1 or 9 may perform the image processing processes described above by receiving the ultrasound image data from the ultrasound diagnosis apparatus, a database in a Picture Archiving and Communication System (PACS), or a database in an electronic medical record system.

Figure 11:
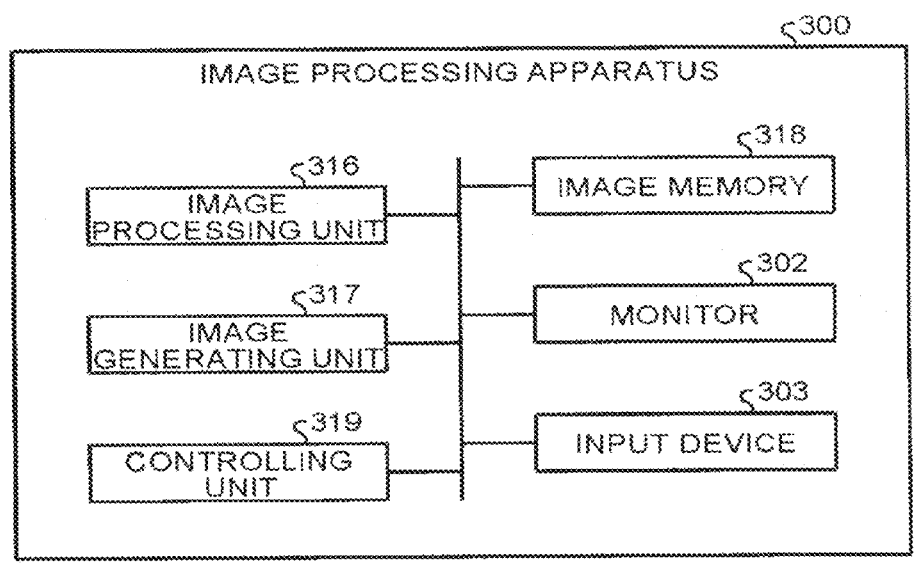
FIG. 11 is a block diagram of an exemplary configuration of an image processing apparatus according to a third embodiment.

FIG. 11 is a block diagram of an exemplary configuration of an image processing apparatus 300 according to a third embodiment. As illustrated in FIG. 11, the image processing apparatus 300 according to the third embodiment includes a monitor 302, an input device 303, an image processing unit 316, an image generating unit 317, an image memory 318, and a controlling unit 319.

The monitor 302 displays a GUI used for inputting various types of setting requests and displays an ultrasound image and the like generated by the image generating unit 317. The input device 303 includes a mouse, a keyboard, a button, a panel switch, a touch command screen, a foot switch, a trackball, and the like. The input device 303 receives the various types of setting requests from an operator of the image processing apparatus 300. The image memory 318 stores therein ultrasound image data and ultrasound images received from the ultrasound diagnosis apparatus, a database in the PACS, or a database in the electronic medical record system. For example, the image memory 318 stores therein ultrasound images and synthesized images generated by the ultrasound diagnosis apparatus. Further, the image memory 318 stores therein ultrasound image data generated by the ultrasound diagnosis apparatus. The controlling unit 319 is a processor that controls the entire processes performed by the image processing apparatus 300.

The image processing unit 316 reads the ultrasound image data stored in the image memory 318 and performs various types of image processing processes thereon. For example, the image processing unit 316 calculates feature amounts from the B-mode data and corrects strain data on the basis of the calculated feature amounts. In another example, the image processing unit 316 calculates feature amounts from power values of tissue Doppler data and corrects strain data on the basis of the calculated feature amounts.

Further, the image generating unit 317 generates a display-purpose ultrasound image by using the data on which any of the various types of image processing processes has been performed by the image processing unit 316.

It is also acceptable to configure the image processing apparatus 300 so as to further include a receiving unit, a B-mode processing unit, a Doppler processing unit, and a strain data processing unit. In that situation, the ultrasound diagnosis apparatus transmits the reflected-wave signals received by the ultrasound probe 1 to the image processing apparatus 300. After that, the receiving unit included in the image processing apparatus 300 generates reflected-wave data, in the same manner as generated by the receiving unit 12 included in the ultrasound diagnosis apparatus. Further, the B-mode processing unit receives the reflected-wave data from the receiving unit and generates B-mode data in the same manner as generated by the B-mode processing unit 13 included in the ultrasound diagnosis apparatus. The Doppler processing unit receives the reflected-wave data from the receiving unit and generates Doppler data in the same manner as generated by the Doppler processing unit 14 included in the ultrasound diagnosis apparatus. The strain data processing unit receives the reflected-wave data from the receiving unit and generates strain data in the same manner as generated by the strain data processing unit 15 included in the ultrasound diagnosis apparatus. Alternatively, the strain data processing unit may generate strain data by using the velocity components of tissue Doppler data generated by the Doppler processing unit.

Other Exemplary Embodiments

In the exemplary embodiments described above, the strain data processing unit 15 is described as calculating the displacement by time-integrating the velocity components of the velocity distribution information obtained from the Doppler processing unit 14; however, possible embodiments are not limited to this example. For instance, the strain data processing unit 15 may generate velocity distribution information by performing a frequency analysis on the reflected-wave data received from the receiving unit 12. In that situation, the strain data processing unit 15 calculates a displacement by time-integrating velocity components of the velocity distribution information generated thereby.

Further, in the exemplary embodiments described above, the image generating unit 17 is described as generating the strain image from the strain data generated by using the strain values corresponding to the degrees of hardness of the tissue in the subject's body and generating the elastography image by using the generated strain image; however, possible embodiments are not limited to this example. For instance, in the elastography mode, another method is possible by which hardness image data is generated by changing the shape of a tissue by using a "push pulse" having high sound pressure and being transmitted from the ultrasound probe 1. Thus, the image generating unit 17 may generate an elastography image by generating a hardness image from the hardness image data and using the generated hardness image. In that situation, the ultrasound diagnosis apparatus includes, for example, a hardness data processing unit as a processing unit that is similar to the strain data processing unit 15. The hardness data processing unit forms a shear wave, which is a transverse wave that propagates through a tissue, and further calculates a propagation velocity $v_s$ of the shear wave. After that, the hardness data processing unit may generate hardness image data (which may also be called "hardness data") on the basis of the propagation velocity $v_s$ of the shear wave. Alternatively, the hardness data processing unit may generate hardness image data by using a Young's modulus that is calculated from the propagation velocity of the shear wave. The filtering process is performed by the image processing unit 16 on the hardness image data generated in this manner by the hardness data processing unit, in the same manner as performed on the strain data.

Further, in the exemplary embodiments above, the example is explained in which the number of levels in the multi-resolution analysis performed by the image processing unit 16 is "3"; however, possible embodiments are not limited to this example. For instance, the number of levels in the multi-resolution analysis may arbitrarily be changed. For example, the number of levels in the multi-resolution analysis may be "2" or "4". Further, in the exemplary embodiments above, the example is explained in which the number of levels in the multi-resolution analysis performed by the image processing unit 16 is two or more; however, possible embodiments are not limited to this example. For instance, the number of levels in the multi-resolution analysis may be "1".

Further, in the exemplary embodiments above, the examples are explained in which the image processing unit 16 extracts the feature amounts from the B-mode data and performs the filtering process on the strain data generated by calculating the strain values and in which the image processing unit 16 extracts the feature amounts from the power values of the Doppler data and performs the filtering process on the strain data generated from the velocity components of the tissue Doppler data; however, possible embodiments are not limited to these examples. For instance, the image processing unit 16 may extract feature amounts from power values of the Doppler data and perform a filtering process on strain data generated by calculating strain values. In another example, the image processing unit 16 may extract feature amounts from the B-mode data and perform a filtering process on strain data generated from the velocity components of the tissue Doppler data. Alternatively, the image processing unit 16 may extract feature amounts from the power values of the Doppler data and perform a filtering process on hardness data or may extract feature amounts from the B-mode data and perform a filtering process on the hardness data.

Further, in the exemplary embodiments above, the example is explained in which the image generating unit 17 generates the strain image by using the strain data generated by the strain data processing unit 15 and generates the elastography image by superimposing the strain image on the B-mode image; however, possible embodiments are not limited to this example. For instance, the image generating unit 17 does not necessarily have to superimpose the strain image on the B-mode image. In that situation, it is acceptable to configure the image generating unit 17 so as to display, on the monitor 2, the strain image and the B-mode image arranged side by side as elastography images. Alternatively, the image generating unit 17 may generate a strain image from strain data and display the strain image alone on the monitor 2. Similarly, the image generating unit 17 may generate the hardness image as an elastography image by using the hardness data generated by the hardness data processing unit and display, on the monitor 2, the hardness image so as to be superimposed on the B-mode image. In another example, the image generating unit 17 may display, on the monitor 2, the hardness image and the B-mode image arranged side by side. In yet another example, the image generating unit 17 may display the hardness image alone on the monitor 2.

Further, in the exemplary embodiments above, the example is explained in which the image processing unit 16 uses the strain image data or the hardness image data generated in the elastography mode as the target of the filtering process; however, possible embodiments are not limited to this example. In other words, the image processing unit 16 may use data other than the strain image data and the hardness image data as the target of the filtering process. For example, in the first embodiment, the image processing unit 16 is described as calculating the edge sizes and the edge directions of the B-mode data as the feature amounts and performing the filtering process on the strain data on the basis of the calculated feature amounts; however, possible embodiments are not limited to this example. For instance, the image processing unit 16 may calculate the edge sizes and the edge directions of the B-mode data as the feature amounts and may perform a filtering process on color Doppler data on the basis of the calculated feature amounts. Further, in the second embodiment, the image processing unit 16 is described as calculating the edge sizes and the edge directions as the feature amounts from the power values of the Doppler data and performing the filtering process on the strain data on the basis of the calculated feature amounts; however, possible embodiments are not limited to this example. For instance, the image processing unit 16 may calculate feature amounts from the power values of the Doppler data and perform a filtering process on color Doppler data on the basis of the calculated feature amounts.

Further, the image processing unit 16 may perform a filtering process on data obtained by color-mapping the "velocities" of color Doppler data. In that situation, for example, the image processing unit 16 extracts the edge sizes and the edge directions from the B-mode data as the feature amounts. After that, the image processing unit 16 performs a filtering process on the data obtained by color-mapping the "velocities" of the color Doppler data, on the basis of the extracted feature amounts. Alternatively, it is also acceptable to configure the image processing unit 16 so as to calculate edge sizes and edge directions from the power values of the Doppler data and to perform a filtering process on the data obtained by color-mapping the "velocities" of the color Doppler data, on the basis of the calculated feature amounts.

Further, the image processing unit 16 may perform a filtering process on data obtained by color-mapping "dispersions" of color Doppler data. In that situation, for example, the image processing unit 16 extracts the edge sizes and directions from the B-mode data as the feature amounts. After that, the image processing unit 16 performs a filtering process on the data obtained by color-mapping the "dispersions" of the color Doppler data, on the basis of the extracted feature amounts. As explained herein, the image processing unit 16 may perform the filtering process while using the edge sizes and directions extracted from the B-mode data as the feature amounts, as long as the image is an image using a different measurement parameter from that of the B-mode data. Alternatively, the image processing unit 16 may calculate edge sizes and edge directions from the power values of the Doppler data as feature amounts and perform a filtering process on the data obtained by color-mapping the "dispersions" of the color Doppler data, on the basis of the calculated feature amounts.

Further, the image processing unit 16 may perform a filtering process on data generated by performing a harmonic imaging process by which harmonic components are imaged. For example, during a Contrast Harmonic Imaging (CHI) process, the image processing unit 16 may apply a filtering process on B-mode data (CHI-purpose B-mode data) generated from reflected-wave data that is obtained by applying a contrast agent to the subject and extracting harmonic components. In that situation, the image processing unit 16 extracts edge sizes and directions as feature amounts from the B-mode data generated from reflected-wave data of fundamental wave components prior to the application of the contrast agent. After that, the image processing unit 16 performs the filtering process on the CHI-purpose B-mode data, on the basis of the extracted feature amounts.

Further, the image processing unit 16 may apply a filtering process on a Tissue Harmonic Imaging (THI) process by which harmonic components are extracted. In that situation, the image processing unit 16 extracts edge sizes and directions as feature amounts from B-mode data generated from reflected-wave data of fundamental wave components. After that, the image processing unit 16 performs a filtering process on THI-purpose B-mode data, on the basis of the extracted feature amounts.

Further, in the exemplary embodiments above, the example is explained in which the image processing unit 16 performs the filtering process on the data available prior to the scan convert process; however, possible embodiments are not limited to this example. For instance, the image processing unit 16 may perform the filtering process by using the strain image or the hardness image available after the scan convert process. In that situation, the strain data processing unit 15 outputs the generated data to the image generating unit 17, and not to the image processing unit 16. After that, the image processing unit 16 extracts edge sizes and directions of the B-mode image available after the scan covert process as feature amounts and performs a filtering process on the strain image or the hardness image available after the scan convert process, on the basis of the extracted feature amounts.

In the exemplary embodiments above, the example is explained in which the image processing unit 16 extracts directionality of the image data as the feature amounts and employs the non-linear anisotropic diffusion filter that performs the smoothing process on the basis of the feature amounts; however, possible embodiments are not limited to this example. For instance, the image processing unit 16 may perform an enhancing process in the directions perpendicular to those of the edges, by employing a non-linear anisotropic diffusion filter. Further, for example, the image processing unit 16 may employ a filter that smooths the image in the directions of tangential lines and that sharpens the image in the directions of normal lines.

Further, in the exemplary embodiments above, it is presumed that the ultrasound probe in which the ultrasound transducer elements are one-dimensionally arranged is used so as to obtain the two-dimensional tomographic image. However, it is also acceptable to obtain a three-dimensional image by using an ultrasound probe in which ultrasound transducer elements that are one-dimensionally arranged are caused to slide or in which ultrasound transducer elements are two-dimensionally arranged. To obtain the three-dimensional image, it is acceptable to apply a two-dimensional filter to each of the cross-sectional planes or to apply a three-dimensional filter having three-dimensional feature amounts.

Further, it is possible to realize any of the processes performed by the ultrasound diagnosis apparatus explained in the exemplary embodiments above, by causing a computer such as a personal computer, a workstation, an image storing apparatus (an image server) in a PACS, an image viewer, and any of various types of apparatuses used in an electronic medical record system, to execute a computer program (hereinafter, "program") prepared in advance. The program may be distributed via a network such as the Internet. Further, the program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, so as to be executed as being read from the recording medium by the computer.

According to at least one aspect of the embodiments described above, it is possible to improve the resolution in the image filtering process, regardless of the types of the image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound apparatus comprising:
a processor configured to
control a probe to transmit and receive an ultrasound wave to and from a subject;
generate first image data based on a first parameter, from a reception signal received by the probe;
generate second image data having an image region of which at least a part overlaps with that of the first image data and being based on a second parameter that is different from the first parameter, from a reception signal received by the probe; and
calculate one or more feature amounts from at least such a part of the second image data that overlaps with the first image data and correct such a part of the first image data that overlaps with the second image data on a basis of the calculated one or more feature amounts,
wherein the processor is further configured to: calculate an edge direction and an edge size of the second image data as said one or more feature amounts from said at least such a part of second image data that overlaps with the first image data and correct said such a part of the first image data that overlaps with the second image data on the basis of the calculated one more feature amounts by smoothing said such a part of the first image data that overlaps with the second image data, excluding parts of said such a part of the first image data that overlaps with the second image data that correspond to tissues exceeding a tissue hardness threshold, along the edge direction, on a basis of the edge size.

2. The ultrasound diagnosis apparatus according to claim 1, wherein the first image data is one of strain image data and hardness image data, whereas the second image data is one of B-mode image data and a power value of Doppler image data.

3. The ultrasound diagnosis apparatus according to claim 2, wherein when the first image data is one of the strain image data and the hardness image data, while the second image data is the power value of the Doppler image data, the first image data and the second image data are generated from mutually same Doppler signals.

4. The ultrasound diagnosis apparatus according to claim 1, wherein the processor is further configured to:
decompose the first image data, by performing a multi-resolution analysis thereon, into low-range decomposed image data and high-range decomposed image data;
reduce an image size of the second image data so as to be same as an image size of the low-range decomposed image data;
calculate, as feature amounts, an edge direction and an edge size in the second image data, from at least such a part of the reduced second image data that overlaps with the low-range decomposed image data, and that smooths such a part of the low-range decomposed image data of the first image data decomposed overlaps with the reduced second image data, on a basis of the calculated feature amounts;
eliminate signals smaller than the calculated edge size as noise, from the high-range decomposed image data of the first image data; and
generate new first image data by synthesizing the high-range decomposed image data of the first image data from which the noise has been eliminated with the low-range decomposed image data of the first image data smoothed.

5. An image processing apparatus comprising:
a processor configured to
generate first image data based on a first parameter, from a reception signal obtained by transmitting an ultrasound wave to a subject;

generate second image data having an image taking region of which at least a part overlaps with that of the first image data and being based on a second parameter that is different from the first parameter, from a reception signal obtained by transmitting an ultrasound wave to the subject; and calculate one or more feature amounts from at least such a part of the second image data that overlaps with the first image data and correct such a part of the first image data that overlaps with the second image data on a basis of the calculated one or more feature amounts, wherein the processor is further configured to: calculate an edge direction and an edge size of the second image data as said one or more feature amounts from said at least such a part of the second image data that overlaps with the first image data and correct said such a part of the first image data that overlaps with image data on the basis of the calculated one or more feature amounts by smoothing said such a part of the first image data that overlaps with the second image data, excluding parts of said such a part of the first image data that overlaps with the second image data that correspond to tissues exceeding a tissue hardness threshold, along the edge direction, on a basis of the edge size.

6. An image processing method comprising:

generating first image data based on a first parameter, from a reception signal obtained by transmitting an ultrasound wave to a subject;

generating second image data having an image taking region of which at least a part overlaps with that of the first image data and being based on a second parameter that is different from the first parameter, from a reception signal obtained by transmitting an ultrasound wave to the subject; and calculating one or more feature amounts from at least such a part of the second image data that overlaps with the first image data and correcting such a part of the first image data that overlaps with the second image data on a basis of the one or more calculated feature amounts, wherein said calculating comprising calculating an edge direction and an edge size of the second image data as said one or more feature amounts from said at least such a part of the second image data that overlaps with the first image data, and wherein said correcting comprises smoothing said such a part of the first image data that overlaps with the second image data, excluding parts of said such a part of the first image data the overlaps with the second image data that correspond to tissues exceeding a tissue hardness threshold, along the edge direction, on a basis of the edge size.

* * * * *